US009501618B1

(12) United States Patent
Wurst

(10) Patent No.: US 9,501,618 B1
(45) Date of Patent: Nov. 22, 2016

(54) SYSTEMS, METHODS AND DEVICES FOR ANONYMOUSLY COLLECTING PERSONAL DATA USING A MOBILE DEVICE

(76) Inventor: Brooke Erin Wurst, Boston, MA (US)

( * ) Notice: Subject to any disclaimer, the term of this patent is extended or adjusted under 35 U.S.C. 154(b) by 919 days.

(21) Appl. No.: 12/698,000

(22) Filed: Feb. 1, 2010

Related U.S. Application Data

(60) Provisional application No. 61/149,511, filed on Feb. 3, 2009.

(51) Int. Cl.
*G06F 7/04* (2006.01)
*G06F 19/00* (2011.01)
*G06F 21/62* (2013.01)
*G06F 21/32* (2013.01)

(52) U.S. Cl.
CPC ......... *G06F 19/322* (2013.01); *G06F 21/6254* (2013.01); *G06F 21/32* (2013.01)

(58) Field of Classification Search
CPC .. G06F 19/322; G06F 21/32; G06F 21/6245; G06F 21/6254; G06F 19/324; G06F 19/327; G06F 19/3443; G06F 19/363; G06F 2221/2111; G06Q 50/24; G06Q 20/40145; H04L 63/0861
USPC ........................ 340/5.81–5.84; 382/115–127; 726/27–28; 705/2–4
See application file for complete search history.

(56) References Cited

U.S. PATENT DOCUMENTS

| | | | |
|---|---|---|---|
| 5,823,948 A * | 10/1998 | Ross et al. | 600/300 |
| 6,185,316 B1 * | 2/2001 | Buffam | 382/115 |
| 6,408,330 B1 | 6/2002 | DeLaHuerga | |
| 7,415,138 B2 | 8/2008 | Schneider et al. | |
| 7,609,862 B2 | 10/2009 | Black | |
| 2002/0081005 A1 | 6/2002 | Black | |
| 2003/0093298 A1 | 5/2003 | Hernandez et al. | |
| 2004/0078217 A1 * | 4/2004 | Bacevice et al. | 705/2 |
| 2004/0177097 A1 | 9/2004 | Yu et al. | |
| 2004/0193448 A1 * | 9/2004 | Woodbridge et al. | 705/2 |
| 2005/0125258 A1 * | 6/2005 | Yellin et al. | 705/3 |
| 2005/0154920 A1 | 7/2005 | Tartaglia et al. | |
| 2005/0160052 A1 | 7/2005 | Schneider et al. | |
| 2005/0229007 A1 | 10/2005 | Bolle et al. | |
| 2005/0246541 A1 | 11/2005 | Ginter et al. | |
| 2005/0278197 A1 | 12/2005 | Podczerwinski et al. | |

(Continued)

OTHER PUBLICATIONS

Zvetco Biometrics LLC, Biometric Fingerprint Software, "A Leader in Biometric Fingerprint Security Solutions", http://www.zvetcobiometrics.com/ 2 pgs, Apr. 22, 2010.

*Primary Examiner* — Muhammad N Edun
*Assistant Examiner* — Nay Tun
(74) *Attorney, Agent, or Firm* — K&L Gates LLP

(57) ABSTRACT

One embodiment of the invention relates to methods and systems for using secure biometric parameters to remotely access electronic databases while rendering the underlying user data, such as patient data, anonymous. Thus, a member of a population, such as person suffering with a disease or infection, can anonymously enroll for treatment or research using a biometric identifier as the sole method of tracking such an anonymous member of a population of interest. The actual research data collected, albeit anonymously, can be acquired at remote locations where the disease is spreading and analyzed at a facility remote from the population of interest. In part, one embodiment of the invention relates to a biometrically secure method of accessing a remote electronic database transmits electronic records using unique biometric features to ensure security.

22 Claims, 14 Drawing Sheets

(56) References Cited

U.S. PATENT DOCUMENTS

| | | |
|---|---|---|
| 2005/0281439 A1 | 12/2005 | Lange |
| 2006/0136744 A1 | 6/2006 | Lange |
| 2006/0293925 A1 | 12/2006 | Flom |
| 2007/0043594 A1* | 2/2007 | Lavergne ............ 705/2 |
| 2007/0047770 A1 | 3/2007 | Swope et al. |
| 2007/0258626 A1 | 11/2007 | Reiner |
| 2007/0279187 A1* | 12/2007 | Hekmatpour et al. ....... 340/5.83 |
| 2008/0072064 A1 | 3/2008 | Franchi |
| 2008/0177569 A1* | 7/2008 | Chen et al. ............ 705/2 |
| 2008/0181465 A1 | 7/2008 | Sauerwein |
| 2008/0191839 A1 | 8/2008 | Sato |
| 2008/0211627 A1 | 9/2008 | Shinzaki |
| 2008/0215890 A1 | 9/2008 | Buer |
| 2009/0006439 A1 | 1/2009 | Joseph et al. |
| 2009/0009284 A1 | 1/2009 | Sako |
| 2009/0019552 A1* | 1/2009 | McLaughlin et al. .......... 726/27 |
| 2009/0021349 A1 | 1/2009 | Errico et al. |
| 2009/0141948 A1 | 6/2009 | Nakaoka et al. |
| 2009/0261947 A1 | 10/2009 | Watanabe et al. |
| 2009/0289761 A1 | 11/2009 | Janke et al. |
| 2009/0309700 A1 | 12/2009 | Fujita |
| 2009/0322477 A1 | 12/2009 | Celorio |
| 2010/0045431 A1 | 2/2010 | Nagamura et al. |
| 2010/0067747 A1 | 3/2010 | Perruchot et al. |
| 2010/0079242 A1 | 4/2010 | Martis et al. |

* cited by examiner

User interface after password verified

PRE-TEST COUNSELLING & QUESTIONNAIRE — 148

GENERAL

How did you hear about this testing session? [Community Center ▼]

Why have you come for a test today?
[To test the application]

Before today, how many times have you been tested for HIV?
[None]

HIV SOCIAL RISK FACTORS

1. How old were you when you first had sex? [    ]
2. (a) Have you ever felt forced into having sex? ☐ Yes ☑ No
   (b) Have you ever forced someone else to have sex? ☐ Yes ☑ No
3. Have you ever had sex for money, food, or clothing? ☐ Yes ☑ No
4. How many different sex partners have you had? [    ]
5. Type of partner? ☐ male ☐ female ☐ both
6. Do you know where you can get condoms? ☐ Yes ☑ No
7. Have you ever used condoms? ☐ Yes ☑ No
8. Do you know how to use condoms? ☐ Yes ☑ No
9. Have you ever used drugs or drank excessive alcohol? ☐ Yes ☑ No

HEALTH AWARENESS

10. To whom do you go for help when you are sick? [doctor ▼]
11. How many times have you had diarrhea this year? [    ]
12. Was it ever bloody? ☐ Yes ☑ No
13. How many times have you had high fevers? [    ]
14. How many times have you seen a medical doctor at a clinic or hospital? [    ]
15. Have you ever had malaria? ☐ Yes ☑ No
16. Have you ever used medications for tuberculosis? ☐ Yes ☑ No
17. Do you use soap every day? ☐ Yes ☑ No
18. How do you think your life would change if you were diagnosed with HIV? [    ]

Informed Consent ☐

VCT Counsellor Assigned [                    ]

[Return]

SYSTEMS, METHODS AND DEVICES FOR ANONYMOUSLY COLLECTING PERSONAL DATA USING A MOBILE DEVICE

RELATED APPLICATION

This application claims the benefit under 35 U.S.C. §119 (e) to U.S. Provisional Application No. 61/149,511 filed on Feb. 3, 2009, the disclosure of which is herein incorporated by reference in its entirety.

FIELD OF INVENTION

The present invention is in the technical field of computers and data collection. More particularly, in part, the present invention relates to systems, methods, and devices for using biometrically secure remote authentication for access to electronic databases.

BACKGROUND OF THE INVENTION

Written records and electronic records are important organizational tools for researchers and practitioners in many fields, such as health care, education, social services, and business management. Traditional written records and electronic records (databases) are only as secure as the media in which they are written. Two significant concerns for many hoping to use database records in remote areas of the world are confidentiality and connectivity.

Using local sources—such as written records or local computer hard drives—for recording sensitive database contents, is not desirable. If the written record is stolen, or the local computer crashes, the security of the data is compromised. Written databases with sensitive data are easy targets for thieves or those hoping to compromise the integrity of the data. The security of and access to electronic databases are subject to several factors—computer hard drive reliability, access to electricity, and the physical integrity of the computer itself, just to name a few.

Therefore, a need exists for devices, methods and systems that address the underlying problems relating to collecting data, from remote locations and populations which desire to remain anonymous.

SUMMARY OF INVENTION

Various embodiments of the invention relate to remote data collection from one or more members of a population using a mobile device and biometric parameters to anonymize the data collection process. These different embodiments represent a remote identification process that is applicable to counseling and collecting data from a population of interest. As a result, certain of the embodiments of the invention relate to remote identification or ("Remote ID") technology. Once collected, a set of anonymous data can be used to generate reports and perform statistical analysis relative to an anonymous or partially anonymous population of interest. Suitable reports include, but are not limited to infection distribution, geographic distribution of a user characteristic, census data collection, population estimates, and others.

Suitable mobile devices that can perform the data collection, data transmission, and biometric parameter collection processes associated with Remote ID technology include smart phones, desktop computers, personal digital assistants (PDAs), laptops, and other portable or substantially portable electronic devices configured to send and receive information. In one preferred embodiment, information that includes patient data associated with a biometric identifier is wirelessly transmitted from a user location to a remote database or remote processing location. That patient data can be used to track an individual's health and treatment regimen by enrolling the patient in a database by which a biometric identifier is used to query the same database and retrieve the patient's anonymous file.

Further, in one general embodiment, the present invention relates to systems, devices, and methods for using secure biometric parameters to remotely access electronic databases. In one embodiment, the methods, devices, and systems described herein can be offered in conjunction with a disease test kit, such as an HIV test, or other kit amenable to use when collecting data from members of a population of interest. By pairing a diagnostic kit or disease test with the system, methods, and devices used to counsel members of a population and collect personal, yet anonymous, information, it is possible to increase the number of tested, treated and tracked individuals as well as the commercial sales volume of such tests or kits.

In one general embodiment, the invention relates to a method of remote data collection and remote user identification. The method is implemented using a computer. The method includes the steps of providing a mobile device that includes a biometric scanner, memory, a display, and a processor; acquiring a biometric identifier from a member of a population of interest using the biometric scanner; collecting personal data from the member of a population of interest; transmitting the personal data; and storing the personal data such that it is indexed using the biometric identifier. The mobile device can be selected from the group consisting of a laptop, a personal digital assistant, a smart phone, a messaging device, or other devices. The biometric identifier can be selected from the group consisting of a fingerprint, a retinal scan, or other personal identifier suitable for scanning and electronic transmission and storage. In one embodiment, the member of a population of interest is an anonymous member of a population of interest. In one embodiment, the method also includes the step of anonymizing the personal data. In one embodiment, the method also includes the step of searching a database that comprises anonymous personal data associated with enrolled members of a population of interest in response to transmission of a fingerprint of an enrolled member. Further, in one embodiment, the method also includes the step of generating a report relative to an anonymous population of interest, each anonymous member of the population of interest having a data file and biometric identifier stored in a database.

In one general embodiment, the invention relates to a mobile device-based individual data collection and transfer system. The system includes a mobile device, the mobile device comprising a transmitter, a receiver, a processor, and a data entry interface; and a biometric scanner, the scanner in electronic communication with the mobile device, the processor for receiving biometric data from the biometric scanner, the processor receiving anonymous personal data generated using the data entry interface, wherein a biometric identifier is generated using the scanner and paired with a set of personal data collected using the mobile device such that the set of personal data can be stored anonymously at a remote location. In one embodiment, the system can include a diagnostic test kit for generating test results such that the test results include an element in the set of personal data. In one embodiment, the system can include an anonymizing module that executes using the processor that processes user data and restricts the transmission of personal identifiable information. In one general embodiment, the system can further include a server and a database, the server comprising software that enrolls members of a population of interest in response to a biometric identifier received from the mobile device, the database storing a plurality of member files, each member file associated with a unique biometric identifier. In one embodiment, the database is searchable using biometric identifier templates of anonymous members of a population of interest. Further, in one embodiment, the data entry interface is programmed to display fields and receive inputs specific to a data collection scheme, the data collection scheme selected from a group consisting of baseline education surveys, user registration, concert admission, medical data collection, census data collection, HIV screening, user enrollment, and data collection relating to a population of interest with sensitive information that requires confidential storage.

In one general embodiment, the invention relates to a method for anonymously collecting information from a member of a population of interest. The method includes the steps of acquiring a biometric identifier from an anonymous member of a population of interest using a biometric scanner; anonymously collecting personal data from the member; associating the member's biometric identifier with the member's personal data; anonymously transmitting the personal data; and storing the personal data such that the personal data is indexed using the biometric identifier such the personal data remains anonymous. In one embodiment, the personal data does not include information about the member's personal identity. The method can further include the step of searching a database that comprises the personal data in response to transmission of a biometric identifier of an enrolled member.

In one general embodiment, the invention relates to a computer system for anonymously collecting information from a member of a population of interest. The computer system includes an electronic memory device; and an electronic processor in communication with the memory device, wherein the memory device comprises instructions that when executed by the processor cause the processor to: convert a biometric identifier acquired from a member of a population of interest into a template; associate the template with anonymous personal data collected from the member; and transmit the anonymous personal data to the electronic memory device. In one embodiment, the memory device includes instructions that when executed by the processor cause the processor to execute an anonymizing module that processes user data and restricts the transmission of personal identifiable information. In one embodiment, the system includes a server and a database, the server comprising software that enrolls members of a population of interest in response to a biometric identifier received from the mobile device, the database storing a plurality of member files, each member file associated with a unique biometric identifier. Further, in one embodiment, the database is searchable using biometric identifier templates of anonymous members of a population of interest.

In one general embodiment, the invention relates to one or more tangible computer readable media encoded with software, the software comprising computer-readable instructions operable, when executed, to cause one or more processors to: convert a biometric identifier acquired from a member of a population of interest into a template; associate the template with personal data collected from the member, the personal data being anonymized such that the member's identity is not transmitted with the personal data; and transmit the personal data to the electronic memory device.

In one embodiment, the software includes computer-readable instructions operable, when executed, to cause one or more processors to execute an anonymizing module that processes user data and restricts the transmission of personal identifiable information.

All of the proceeding embodiments can be combined together individually or in the aggregate and all such embodiments are within the scope of the invention. In addition, all methods and techniques described herein can be implemented as stand alone methods or as a processor-based system or method. In one embodiment, such a system includes an electronic memory device; and an electronic processor in communication with the memory device, wherein the memory device comprises instructions that when executed by the processor cause the processor to execute one or more of the method steps described herein.

BRIEF DESCRIPTION OF THE DRAWINGS

Various embodiments and other aspects of this invention will be readily apparent from the detailed description below and the appended drawings, which are meant to illustrate and not to limit the invention, and in which:

FIGS. 4A-D are a series of screenshots showing exemplary user interfaces relating to patient identification screens, as well as pre-test, screening, and post-test questionnaires in accordance with an embodiment of the invention.

DETAILED DESCRIPTION

Figure 1A:
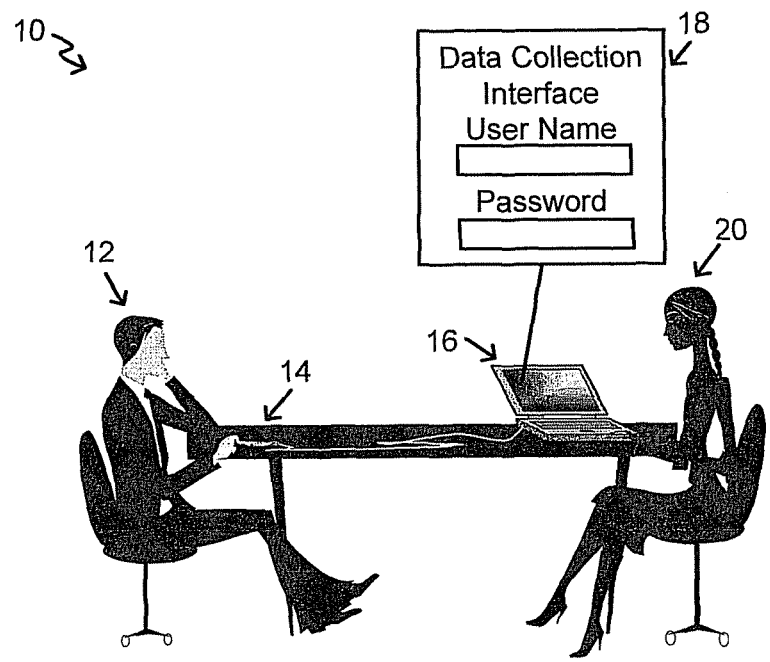
FIG. 1A is a diagram of a system user counseling a member of a population of interest and signing in to a data management system, in accordance with an embodiment of the invention.

The following description refers to the accompanying drawings that illustrate certain embodiments of the present invention. Other embodiments are possible and modifications may be made to the embodiments without departing from the spirit and scope of the invention. Therefore, the following detailed description is not meant to limit the present invention, rather the scope of the present invention is defined by the claims.

It should be understood that the order of the steps of the methods of the invention is immaterial so long as the invention remains operable. Moreover, two or more steps may be conducted simultaneously or in a different order than recited herein unless otherwise specified.

The use of sections or headings in the application is not meant to limit the invention; each section and heading can apply to any aspect, embodiment, or feature of the invention.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The terms "a," "an," and "the" mean "one or more," unless expressly specified otherwise.

The foregoing, and other features and advantages of the invention, as well as the invention itself, will be more fully understood from the description, drawings, and claims.

In various physical and social sciences, field researchers, medical practitioners, and other data collectors are often limited to data contained in their own written records, on their own computer hard drives, or on remote databases requiring both an Internet-enabled connection and electricity. With confidentiality a growing concern as the use of electronic databases increases, the need for security has become urgent in various data collecting scenarios. Further, in light of user sensitivity to the dissemination of personal information, there need to be safeguards to anonymously obtain data while facilitating follow-on research and interactions with the anonymous provider of the data. In the case of a data providing user or subpopulation member that is seeking treatment, such as alcoholics, AIDS patients, drug users, and others with sensitive conditions, the need for anonymously enrolling users while enabling identification of the anonymous users is great.

Those seeking to use electronic databases in remote locations are often at a disadvantage because in much of the world there is no direct access to electricity or the Internet. However, there is wide penetration of cellular signals. Cellular signals can be used to transmit and transfer electronic information. Yet even with seemingly secure cellular data transfer, traditional data is not always secure and can become compromised.

At a general level, the invention relates to remote identification of members of a population of interest such that confidential personal data associated with one or more of the members can be collected and stored in a secure manner. In some embodiments, the data is securely transmitted to one or more central databases. In some embodiments, the invention provides a mobile, biometrically-secured confidential access system designed to permit controlled access to medical records from anywhere there is a cellular signal, a data transmission network, post for mailing disks, and/or internet access. In particular, the system is ideally suited to use in extremely rural or remote areas where lack of electricity is an impediment to creating, accessing, and maintaining electronic medical records. The embodiments described herein provide for security and confidentiality with respect to the personal data for a given member of a population of interest. In some embodiments, fingerprints are used as the only identifier for certain database records, such as certain "front end" records. Thus, a member of a population is treated (or otherwise interacts with the system) anonymously, although counterintuitive, by using a personal biometric identifier in lieu of a name or government issued identifying number.

In one embodiment, the invention allows for the anonymous collection of information from a subject (e.g., a patient) or a group of subjects (e.g., HIV patients or drug users). Specifically, rather than providing a name, social security number, or other personal identification, a subject instead provides a biometric identifier, such as a fingerprint, which is associated with that subject's file. The subject's name or other identifying information may never be provided and, if provided, is not associated with the biometric identifier. Thus, the subject's identity remains anonymous and independent of the biometric identifier.

Using a biometric identifier in this way is akin to assigning a random identifier to the subject. However, a biometric identifier has significant advantages over a random identifier (e.g., a number, bar code, wristband, RFID, etc.) since a random identifier can be easily lost, misplaced, forgotten, damaged, or misappropriated. By using a biometric identifier, the subject necessarily brings the requisite authentication to every consultation, thereby permitting seamless and anonymous updating of the subject's file. Moreover, since subject names or other personal identifiers are not necessary, valuable data (e.g., demographics, health status, prevalence of substance abuse, response to treatment) can be distributed to third parties (e.g., researchers, health care providers) while maintaining complete subject anonymity.

Thus, as an example, if the population of interest includes people in a remote location that may be suffering with HIV, a mobile device with a biometric scanner can be used to collect data from the population of interest and relay that data via a wireless link to a remote database. Further, the recorded personal data can be mined/used/analyzed by designated researchers from a "back end" perspective without compromising the anonymity and confidentiality of the members of the population of interest. If the population of interest includes drug users, single mothers, adopted children, homeless people, clinical trial participants, criminals, or other classes of individuals, personal or cultural barriers of confidentiality and security can make people unwilling to cooperate or volunteer personal information. The present invention overcomes many data collection issues and allows health care workers to anonymously collect information, treat, and track individuals, and gives researchers an opportunity to access larger pools of data.

In FIG. 1A, an implementation of the method and the associated system and devices suitable for collecting personal information and a biometric identifier at a remote location is shown. Specifically, as shown in FIG. 1A a health care worker, shown on the right, is counseling a member of a population of interest (such as a patient) on the left. In some embodiments, after a health care worker signs in using encrypted password, the patient places his fingerprint on a USB fingerprint scanner, which then displays the image in a browser-based window. The user "submits" the image of the fingerprint embedded in the URL via the Internet generally via a device connected to a cellular phone network or other network (e.g., using a smart phone or cellular modem, network interface device or wireless data card inserted into or connected to a laptop computer). The remote/central server, using the present invention, searches through the already captured fingerprint image/medical record database for a match. If a match is found, the patient history (or other information in an enrolled user's file or fields) is displayed back as a URL-based record. If no match is located, the user enrolls the patient's fingerprint as a new record in the central database and is ready to create new fields of data relative to screenings/visits/etc.

At future appointments, once the patient "signs in" to the system with his fingerprint, health care providers can access the patient's medical history by clicking on previous appointment dates. In one embodiment, these clickable dates are functionally URLs that connect to the data collected on the previous appointment.

In general, embodiments of the invention use various communication protocols and networks to collect certain categories of data associated with, resident on, captured using, or otherwise generated by a user's mobile device or a substantially mobile device, such as a desktop computer. In addition, embodiments also relate to the use of any type of data that is processed remotely in response to data sent from the mobile device. As a result, the embodiments of the invention relate to any type of data suitable for use by mobile devices and processors. The data can include, but is not limited to any suitable type of data such as metadata, personal data, device-generated data, user-generated or inputted data, and various types of derived data, all of which may be the same, different, or overlap with respect to data type in some embodiments. In one preferred embodiment, the data of interest is personal data associated with a patient suffering from a disease or condition.

The advantages of the present invention include, without limitation, that it is portable, easy to transport, and provides electronic access to confidential data through various access and searching mechanisms. It is straightforward to move and utilize devices that implement Remote ID technology anywhere on Earth where there is access to the Internet or cellular telephone signal.

An existing individual record may be queried by launching the client application, presenting a fingerprint, a template associated with a biometric identifier, or other biometric scan and having the server retrieve a matched record and display/transfer it to the remote client.

Various embodiments provide access to individual or aggregated records through one or more query/search functions. In one embodiment, an authorized user may select a function within the client or server application that requests the export of a specific record or range of records that meet user-entered search criteria (for example, contents of specific fields, ranges of values in specific fields, as examples.) In another embodiment, an authorized user may request an export of all or specified records, ranges of records, etc., into an extant database application such as Oracle, SAP, MS Access, MySQL, etc., or statistical analytics application such as SPSS, JMP, etc.

Figure 1B:
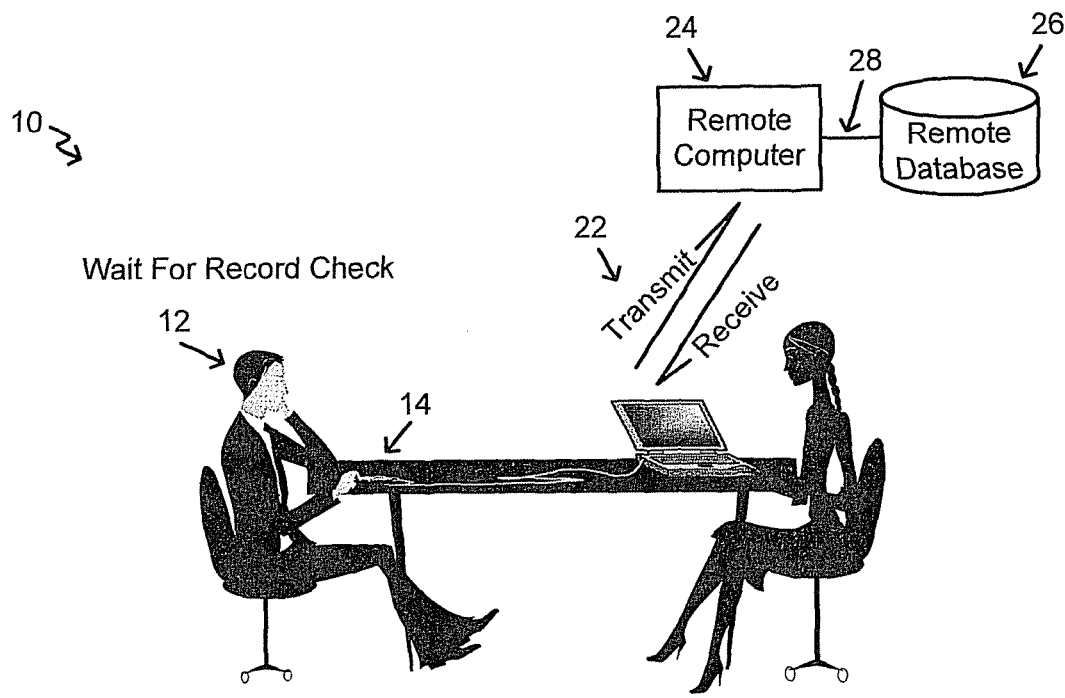
FIG. 1B is a diagram depicting data transfer between a local computer and a remote computer and/or remote database, in accordance with an embodiment of the invention.
Figure 1C:
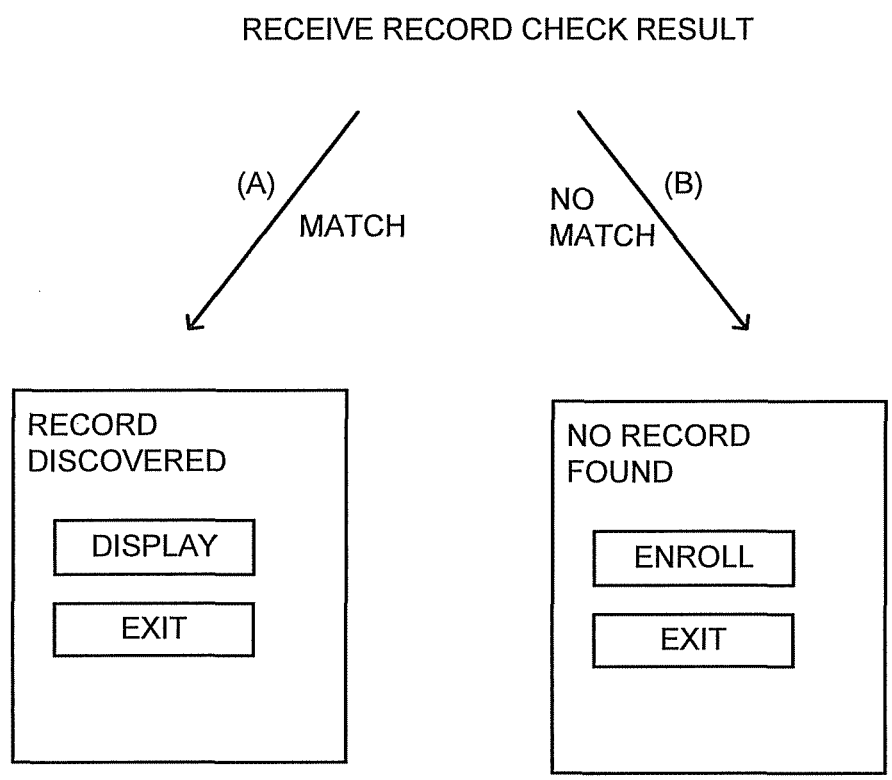
FIG. 1C is a flowchart of a record check result, in accordance with an embodiment of the invention.
Figure 2:
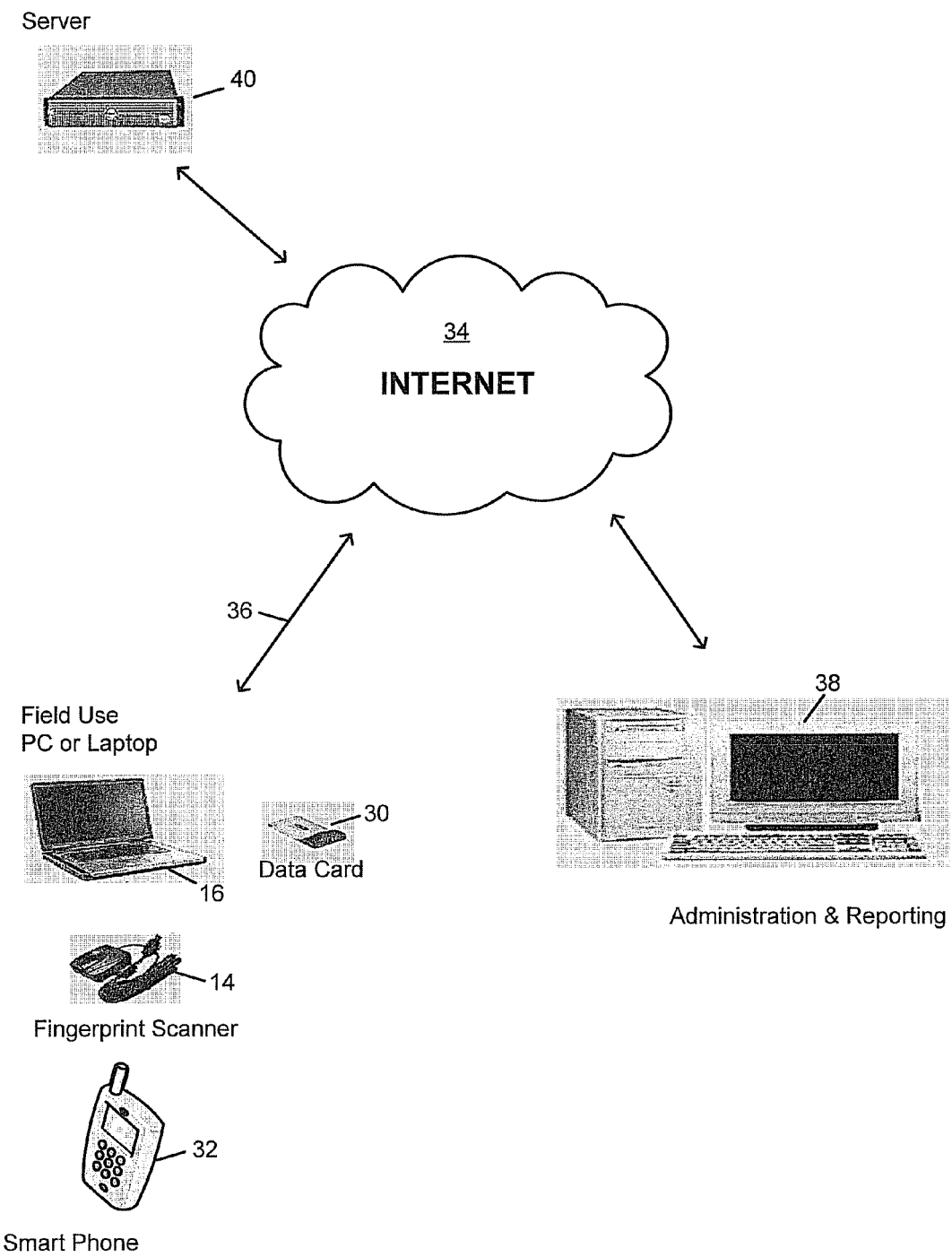
FIG. 2 is a diagram of a network-based system, in accordance with an embodiment of the invention.

Referring to FIGS. 1A to 2, there is shown how an exemplary anonymous Remote ID system 10 works in a real world enrollment or data collection scenario, in accordance with an illustrative embodiment of the invention. In FIG. 1A, an encrypted local computer, smart phone or other suitable mobile device 16 requires authentication by an authorized user (e.g., a researcher, doctor, health care worker) 20 using, for example, a user name and password are received by an interface 18. The mobile device, such as a laptop 16, is in communication with a biometric scanner (e.g., a USB fingerprint scanner, built in scanner, or other scanner) 14. Once the user 20 has signed in, the patient (or member of a population of interest) 12 provides a biometric identifier, such as a fingerprint, to the biometric scanner 14. The present invention, using the biometric identifier, associates the patient's biometric identifier with the patient's medical information located in a central database. In some embodiments, the user 20 collects medical information from the patient before or after the patient provides a biometric identifier. In other embodiments, the user can retrieve patient information which was previously collected when the patient was enrolled or at a time after enrollment. Thus, the patient's biometric identifier can be used to create, store and retrieve the patient's personal information from the encrypted local computer or from a remote computer or database. Software, programmable logic or other types of computer instructs are resident in memory in the devices 22, 24 shown in FIG. 1B to capture, transmit, and process the relevant biometric data and user 12 records.

FIG. 1B shows communication of information 22 between a local computer 16 and a remote computer 24, in accordance with an illustrative embodiment of the invention. The remote computer 24 can be in further communication 28 with a remote database 26 which stores personal data, such as patient medical information and/or makes it available to system users.

FIG. 1C shows a flow chart of a patient record check, in accordance with an illustrative embodiment of the invention. After the patient provides a biometric identifier, the computer then searches the database (either local or remote) for a matching biometric identifier already on file. If a matching record is discovered, the user is given the option of displaying the patient's record or exiting from the system. If a matching record is not found, the user is given the option of beginning the patient enrollment process (creating a new record in the database) or exiting from the system.

When results of the biometric identification reveal that a patient is a new patient (i.e., previously unenrolled), a new patient screening session is created. In one embodiment, creating a new screening session includes the step of entering data into each form in order (pre-screening questionnaire, screening and post-screening questionnaire).

FIG. 2 shows an exemplary computer system in greater detail. A suitable mobile device 16, such as a field use personal computer, smart phone, or laptop, is in communication with a biometric scanner 14, such as a USB fingerprint scanner, which is used to obtain a unique biometric identifier from a patient. The mobile device can include a data card 30 or other storage device for locally storing information, such as patient records. In one embodiment, a smart phone 32 with a built in biometric scanner can be used to perform remote and anonymous data collection with respect to a population of interest. In one embodiment, a diagnostic test kit (not shown) is also used to collect information that is then stored anonymously.

In addition, the mobile device can also be capable of connecting to the Internet or a network 34 using a wired or, more preferably, a wireless 36 connection. Through the Internet and/or network 34, the mobile device 16 is able to communicate with other computers or secondary mobile devices. For example, the mobile device can communicate over the Internet 34 with an administrator 38 for processing and reporting purposes. The database and the relevant programmable logic or software modules to facilitate the Remote ID process and other processing and data display steps can be resident on the administrator computer 38 or the server 40. The mobile device can also connect to server 40 (e.g., a Windows based server), such as a data server or another computer to upload or download patient records.

Figure 3A:
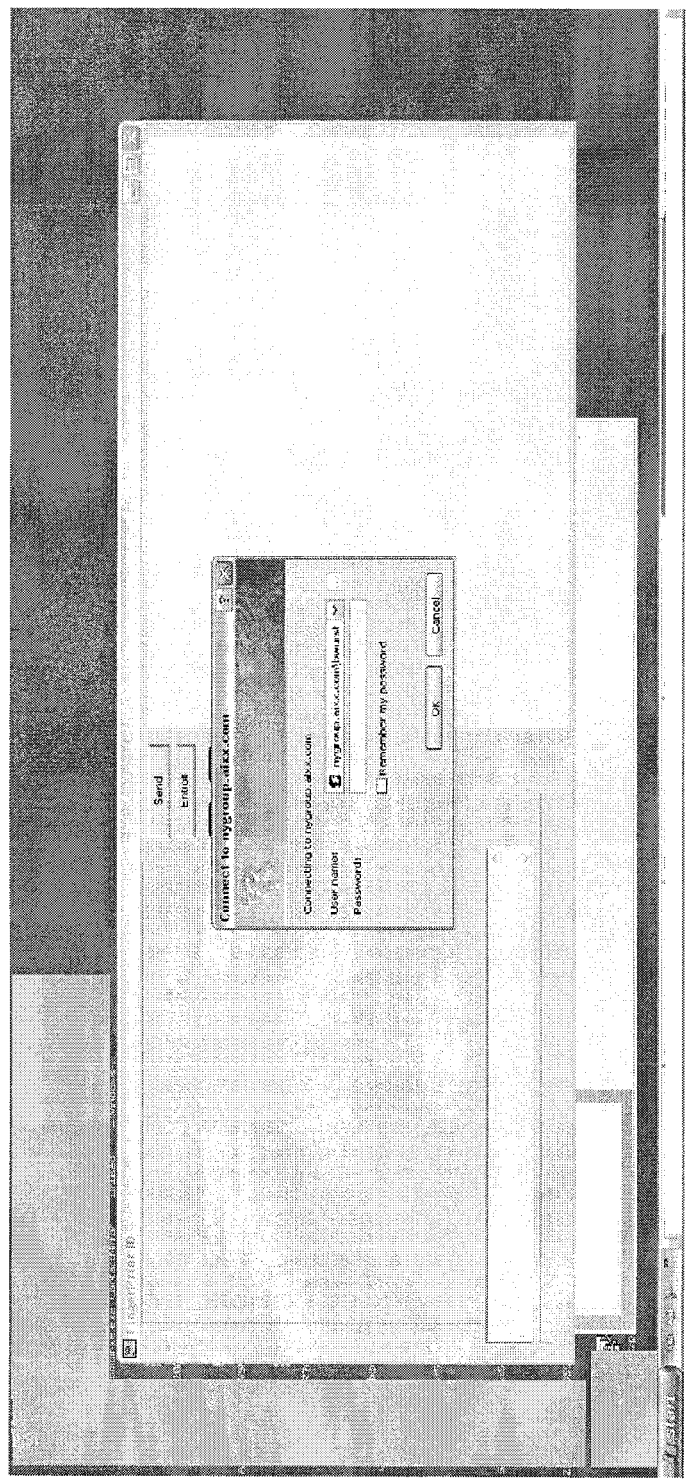
FIGS. 3A-J are a series of exemplary screenshots of user sign in, fingerprint scanning, record retrieval, and patient counseling, in accordance with various embodiments of the present invention.

FIG. 3A shows an exemplary login screen displayed on the mobile device, in accordance with an illustrative embodiment. To authenticate (i.e., sign on) to the system, a user enters a username and password to access the system and pass through the first level of security. The mobile device transmits the patient's biometric data by, for example, a URL to a remote server and the remote server retrieves any matching records and displays the records on the mobile device. Because, in one embodiment, the patient's biometric identifier is used to identify the patient's records, the patient's name and social security (or other patient specific identifier, index, or tracking device) number are never displayed because no personal identifiers other than gender and year of birth are taken. If no records match the patient's biometric identifier, the user is given the option of creating a new record in the database, i.e. enrolling the patient.

Hardware/Software Components

In various embodiments, reference is made to a workstation, as used herein the term is interchangeable with any mobile device or fixed device (or combination of devices or subsystems) suitable for capturing information from a member of population of interest and generating a biometric identifier associated with such member (or user). In one preferred embodiment, the workstation is a computer, smartphone or a laptop that is in electronic communication with a biometric scanner.

The workstation (remote mobile device or data capture device) and central server applications can be programmed and ported between various commercial and publicly available programming languages. Alternatively, certain features of the remote identification described herein can be implemented using an application specific integrated circuit. One embodiment described herein is written in Borland's Delphi incorporating function calls to Griaule Biometric's Fingerprint SDK. Other embodiments can use Griaule's Linux SDK, VeriFinger Linux SDK and others. Various other biometric identifier specific SDKs can be used as appropriate to collect fingerprints and other identifiers for use with the systems and methods described herein. However, other biometric software, middleware, open source software, freeware and SDKs can be used in various embodiments. The Griaule code performs the scan to image, image to vector and vector compare functions. In one embodiment, as used herein the term "vector" refers to any matrix or array of data. In another embodiment, the term "vector" refers to mathematical relationships between points and the paths connecting them to describe an image. Thus, in one embodiment biometric identifiers are imaged as vector graphics that include one or more paths (or the points that form such paths).

In one embodiment, the other aspects of the application are either performed by the Delphi code (or other applications or software modules) or by using web based PHP scripting. In one embodiment, there are two distinct software applications; one for the workstation and one for the server. Certain features of these programs are described below.

In one embodiment, the workstation or mobile device includes or otherwise interfaces with an anonymizing module resident in local or remote memory storage that executes using a processor included within the mobile device that processes user data and restricts the transmission of personal identifiable information.

The Workstation/Mobile Data Capture Elements

Comprising a Windows (XP, Vista, 7, Mobile, CE) or Linux operating system based PC or other remote device, such as a Smartphone, tablet or PDA running under various mobile operating systems such as: Windows Mobile, Symbian, Linux, Palm, or WebOS, a fingerprint (or other biometric) scanner and customized Remote ID workstation application, the workstation is used to capture, insert, retrieve and edit data from a server based on the identified fingerprint (or other biometric identifier). The workstation application scans and captures a fingerprint or other biometric identifier, determines the quality of the scan (allowing for rescanning if the scan is not optimal), converts the fingerprint or biometric image to template and sends the template to one or more servers via an Internet connection.

If the server application finds the fingerprint, biometric identifier, or scanned template in the database, the database record is opened and appropriate information is returned to the remote workstation to view or edit. If the server application fails to find the scanned template a new template and record can be added to the server's database. In one embodiment, the scanned template is a vectored template that includes a digitized vector image of the biometric scan. In another embodiment, the reference to a vector refers to a row, column, or other m by n array or matrix that encodes numerical data that is correlated with a biometric identifier. Operation of the workstation typically includes a mobile device, a biometric scanner, and Internet connectivity (laptop cellular modem Wi-Fi, etc.).

Remote or Local Server/Remote Data Storage and/or Processing

In one embodiment, fingerprint or other biometric template and form data reside on a central server. When a workstation connects to the server and sends the fingerprint or biometric identifier (or an associated template) the anonymous remote identification server application searches the database for a match. If a match is found, the workstation is sent the appropriate information associated with the anonymously identified records. If no match is found, the workstation user has the option of creating a new database record, e.g. enrolling the new data. The server can be run on, by way of non-limiting example, Windows 2000, Windows 7, XP, Vista, 2000 Server, 2003 Server or any derivative. Typically, it runs on a web server (IIS, Apache, etc), PHP and has a persistent Internet connection. In the present embodiment, the data is maintained in a Microsoft Access database, but can be migrated to any ODBC compliant database application or system.

Additional details relating to the operation of an exemplary system implementation are provided below as a collection of exemplary method steps. The method steps need not necessarily be performed in the sequence recited below. In one embodiment (using fingerprint scan as the biometric identifier), the sequence of user events or software events may include some or all of the following steps:

1. An Internet connection is established.
2. A software application or module is executed.
3. A software application or module connects to the central server's web server or other application of interest.
4. User is required to log on using a secured log-on and password.
5. The main software application page is displayed.
6. When a finger is presented to the scanner, the finger is scanned and the fingerprint appears on a display along with a quality indicator (red=bad, yellow=marginal, green=good). The Griaule SDK performs the scan and creates a fingerprint template. It also returns the scan quality value that is converted to a simple displayable color indicator by the software application or module.
7. The finger can be rescanned until a good scan is obtained by simply removing the finger and re-presenting the finger in the scanner.

8. Once an acceptable scan is obtained, the user presses the Send button, initiating the transmission of the vectored template to a remote or local server.
9. The workstation waits for a response from the remote or local server.
10. The server accepts the connection, receives the template and compares it against the templates in the database. If a match is found, the server sends the workstation a unique ID for the matched record. If a match is not found, the server responds with a 'not found' code.
11. If the server responds with a 'not found' code, the workstation then connects to a server's web server and opens an Enroll page allowing the user to add the new fingerprint (scanned template) and associated data to the server's database.
12. If the server responds with an ID (such as existing database record, data set, or file), the workstation requests the detailed data page for that individual whose fingerprint (scanned template) matched.
13. Once the transaction is complete and the workstation has received a response from the server, the workstation disconnects from the server.

At this point, the user can navigate throughout the identified individual's data using a web-based interface, such as browser, terminal, client, or other suitable interface. The structure and content of the stored data can be customized for the specific application. One application is for HIV screening where the database contains questionnaire responses, HIV test results and demographic information. Patient anonymity is maintained because the system uses the fingerprint scanned template for identification and no other identifiable information (name, address, etc.) is necessary. As a result an anonymizing step is performed in the course of collecting data from certain populations of interest. In another embodiment the anonymizing step is automated such that algorithms or data routing is used such that even if personal information is collected along with the biometric identifier, such information is separated from the data or processed in a manner such that only certain users have access to such personal identifiers.

Since the fingerprint scanned template (or other biometric identifier) and the web-based forms database scripting are segregated, both the workstation and server applications can be customized for any use where biometric identification is desired (or necessary) to create or maintain database information. In one embodiment, a Delphi-based application, a Java-based application, or another software module is used for obtaining a fingerprint (such as with a scanned template) as data (using the workstation), sending the fingerprint (as data or a scanned template) using a workstation and searching fingerprints in the form of a collection of scanned templates (or other indexed data) stored at a remote server while the PHP/web interface uses the identification from a software application, such as a Delphi application, Java-based application, etc. to store and retrieve data in the database. In one embodiment, once a fingerprint/biometric identifier (scanned template) has been identified the PHP/web interface manages whatever data is desired to be stored.

Thus, in one embodiment, since no data is permanently stored on the local workstations, this arrangement significantly reduces the risk of loss or exposure of personal data. The exception to this occurs when, upon the workstation's lack or loss of an Internet connection of any type, the workstation automatically executes an 'off-line' mode, which permits the workstation to capture and store both the scanned template and associated acquired data, which are then automatically transmitted to the central server and deleted from the workstation upon re-establishment of any Internet connection.

In addition, in other embodiments report generation and other types of reporting functionality and data mining modules are part of the system and method embodiments. The reporting features of the invention are integrated with the functionality of the database. The present embodiment includes methods, processes, and programming for authorized users to search and query the created database(s) to create and retrieve report(s) generated by interaction between a workstation device and the server, such that the data can be retrieved from any to all individual records based upon the query criteria. One example of a report showing information collected using Remote ID technology for a population of interest is provided below as Report Example I.

In part, the present embodiment includes a 'query template generation' function, permitting an authorized user or administrator to create and/or save a specific set of criteria. Those criteria may be any single or combination of named or otherwise identified fields included in the database. For example, using the present illustrative embodiment, a researcher evaluating the efficacy of a specific educational or medical intervention can create a query and generate a report based upon any or all individual patients who participated in an interventional HIV program and the results of each subsequent HIV test. The present embodiment, and, more generally, any embodiment of the invention, permits the authorized user to name and save the report to a specified server location or to the connected workstation device and then, using standard analytic tools, apply statistical methodology to the reported data, in the present example, to assess potentially differentiable outcomes of the interventions.

Exemplary Screen Shots/Graphic User Interface Embodiments

Various aspects of the invention can be understood relative to certain screen shots and graphic user interface displays. An exemplary collection of such screen shots and interfaces follow. Although in this illustrative embodiment the screenshots reference HIV testing, these are but exemplary templates and can be configured for anonymously enrolling new individuals and securely storing and retrieving information for various other populations of interest.

Referring to FIG. 3A, an exemplary login screen is shown. To authenticate (i.e., sign on) to the system, a user enters a username and password to gain access to the system.

Figure 3B:
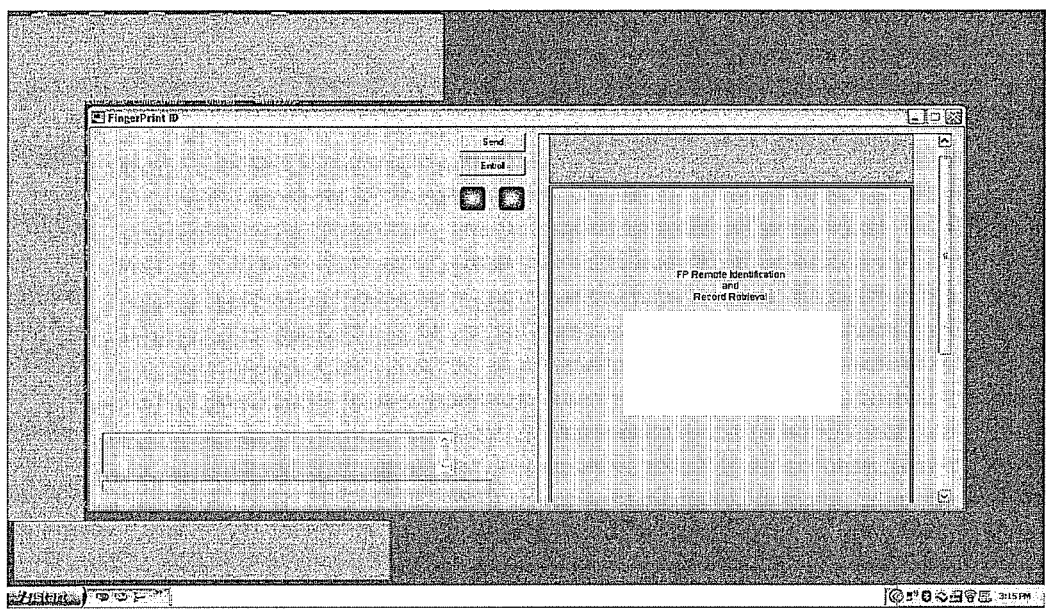

Referring to FIG. 3B, an exemplary opening screen is shown. A user is asked to log in prior to arriving at this page. The left side of the workstation application is a window to the Griaule SDK that, in this embodiment displays the fingerprint scan, while the right displays data via a web interface from a processor-based device, such as a server. One exemplary server is a central server that is programmed with or has remote identification software installed that can receive biometric data and query a database of enrolled members while being able to enroll new members and perform analysis relating to the underlying data. In one embodiment, data analysis can be performed at a workstation remote from the server by running statistical software packages relative to an anonymous data set collected from a population of interest to generate social, medical, treatment, disease trajectory, and other reports of interest.

Figure 3C:
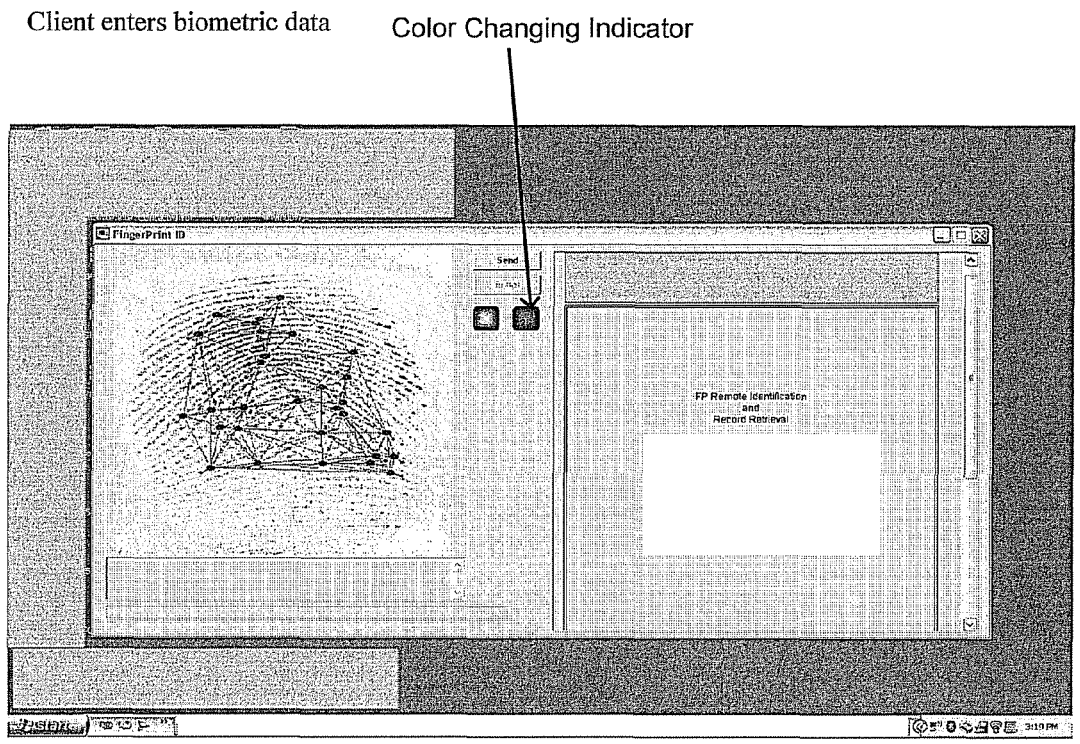

FIG. 3C shows an exemplary fingerprint scan. When a finger is presented to the fingerprint scanner, the Remote ID software creates a vectored map (template) of the scanned image. Here, the process of vectorizing the image is performed by the Griaule SDK. Specific points in the image are identified and their relative position measured and documented. The higher the detail present in the image, the more points in the image that can be identified. The client application can be configured to the specific number of biometric reference points desired; the greater the number of reference points, the more unique or discrete the record. The program can be configured to indicate whether or not an acceptable quality fingerprint scan has been obtained.

Figure 3D:
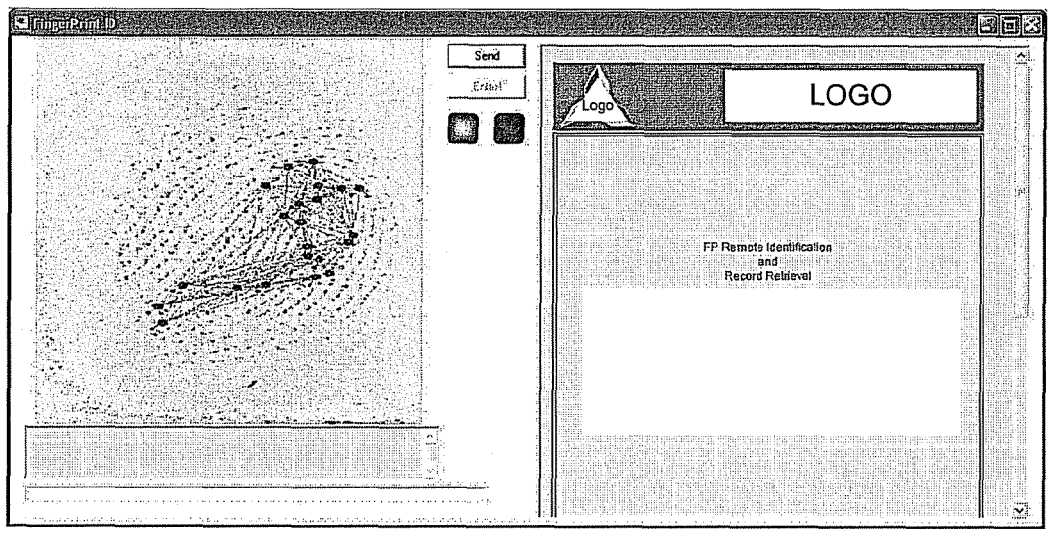

For example, FIG. 3C shows that the fingerprint scan was acceptable by the color changing indicator in the center column. As shown in FIG. 3D, an indicator in the center column indicates a poor scan and is considered unacceptable to submit for a match search. In one embodiment, such a match search or matching query is performed using a local or central database. A color changing indicator or symbol will be displayed when a scan is marginal but allowable.

A finger scan can be repeated as easily as removing the finger from the scanner, then presenting to the scanner again. When a good scan is achieved, the data can be sent to the Remote ID server for matching. The Remote ID application will transmit the scanned fingerprint template data created by the Griaule SDK to the Remote ID server in response to clicking on the SEND button in the center column of an interface displayed using the workstation application. As is the case throughout the embodiments described herein, various interface details are provides as non-limiting examples.

Figure 3E:
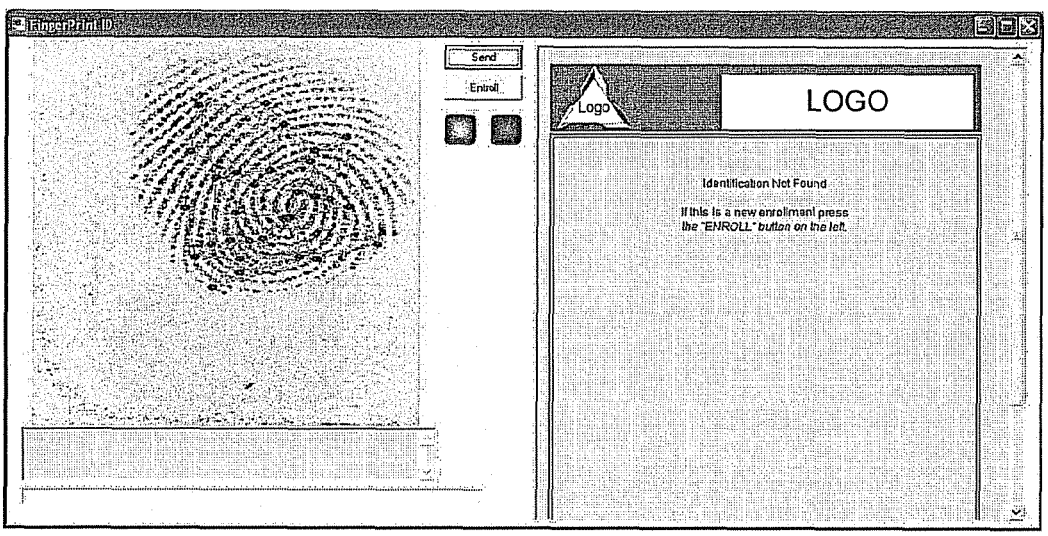
Figure 3F:
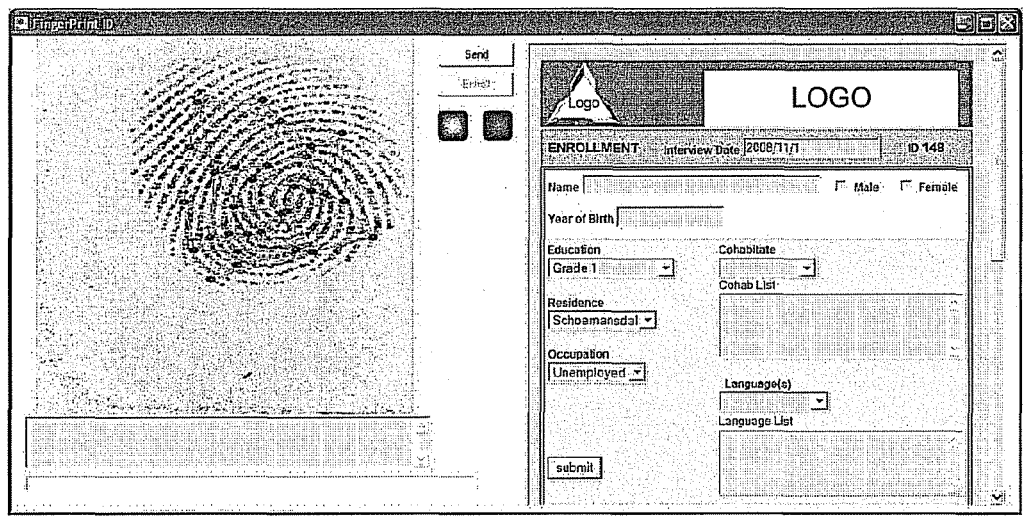
Figure 3G:
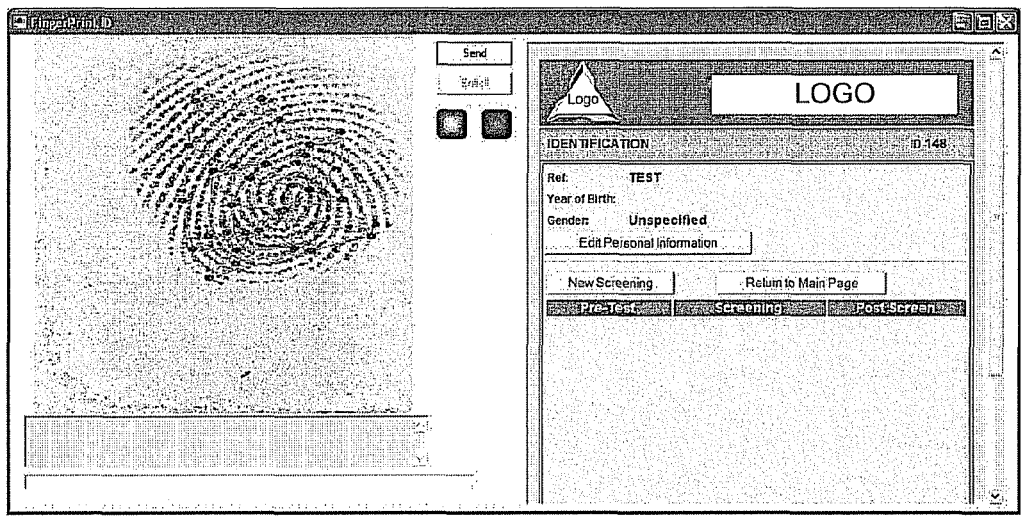
Figure 3H:
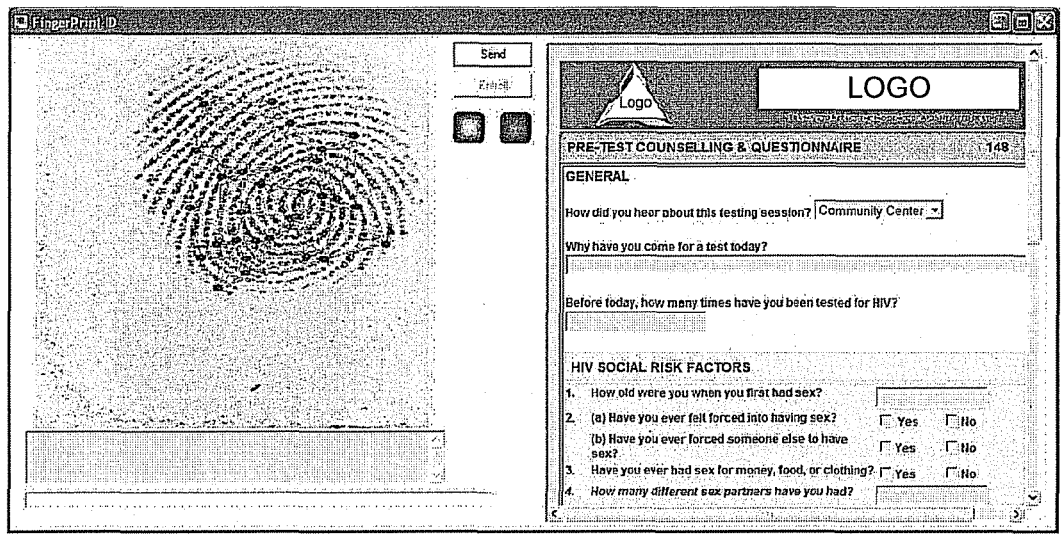
Figure 3I:
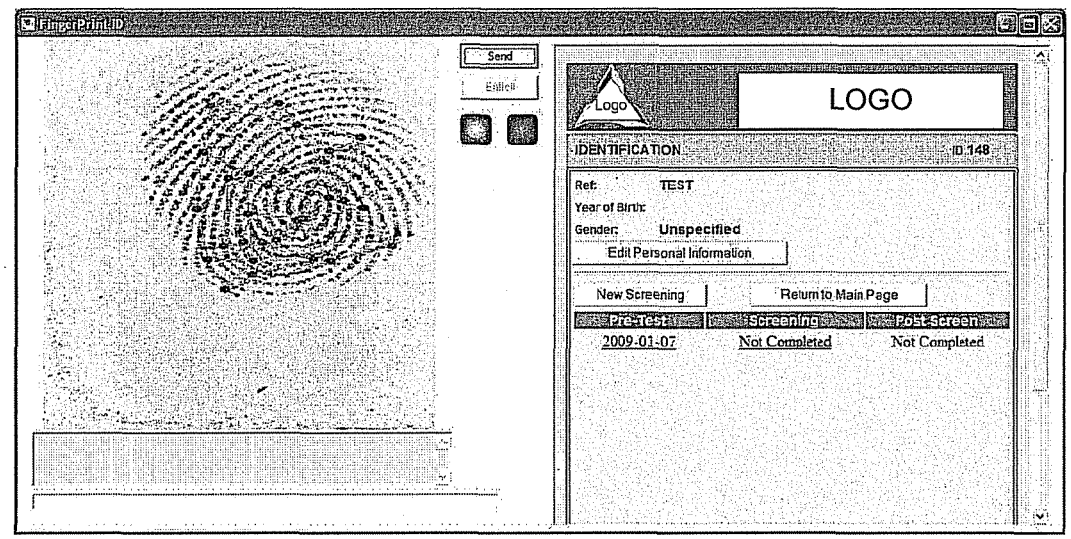
Figure 3J:
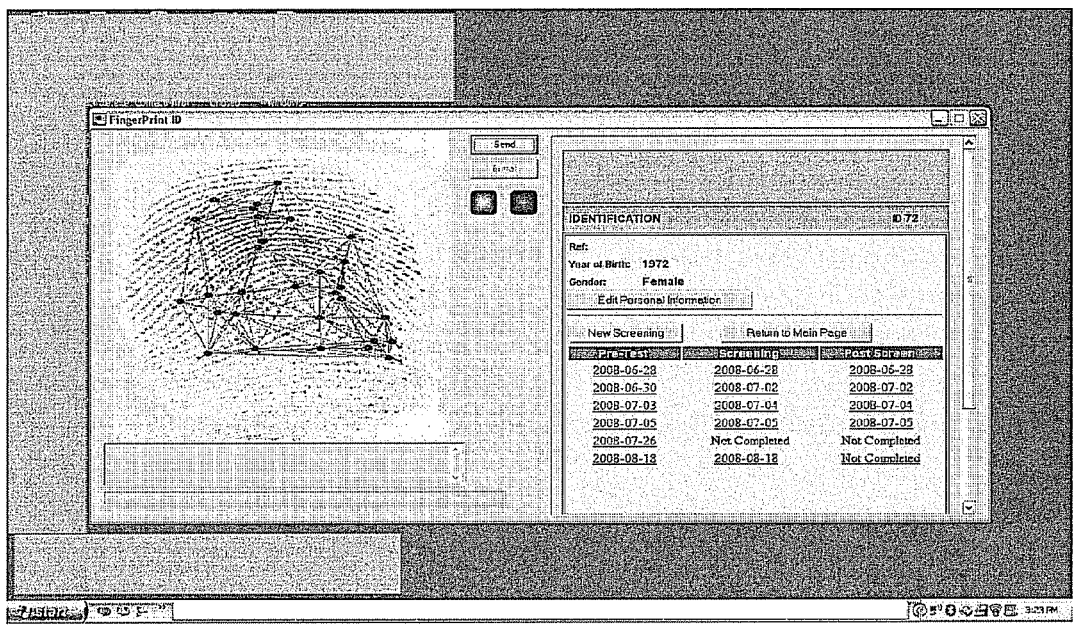

Referring to FIG. 3J, in one embodiment, if the fingerprint data is found in the database, the individual's prior record(s) are retrieved and displayed. In one embodiment, the user transmits biometric data via a URL to a remote server. In turn, the remote server retrieves and displays client/patient records. In one embodiment, no name, SS#, or other client identifier is displayed because no personal identifiers other than gender and year of birth (YOB) are taken.

As shown in FIG. 3E, in one embodiment, if the fingerprint data is not found in the database, the RemoteID application returns a message and allows the user to add (enroll) the new individual's fingerprint (scanned template) to the database.

Referring to FIG. 3F, in one embodiment, an exemplary first screen in the enrollment process is shown. The enrollment process creates an entry in the database for the new individual. Demographic data is requested and associated with the fingerprint data. This becomes the main entry in the database for this individual.

Referring to FIG. 3G, in one embodiment, once the new individual's data is submitted, the user is offered additional data management options to add (in this embodiment) a new HIV screening session and to edit the demographic data. This page can also be displayed when an existing fingerprint is identified. Any previous HIV screening sessions (or other data records) are displayed and the user can review existing data or begin a new screening session.

In this exemplary embodiment of the invention, each screening session is divided into three sections and is typically completed in order; the pre-screening questionnaire, the HIV screening and the post-screening questionnaire. An exemplary data acquisition form, a pre-screening questionnaire page, is shown in FIG. 3H.

Once each session (data collection) segment is completed it is time stamped and committed to the database. The user progresses in the pre-test, screening, post screening order as shown below. As shown in FIG. 3I, the individual has completed the pre-test questionnaire, but not the screening or post-test screening.

In one embodiment, the only way to view data for a particular individual is for that individual to have his fingerprint scanned and sent to the server. As shown in FIG. 3J, if the server finds the scanned template, various types of information are delivered to a computer or the workstation. In one embodiment, after a successful query and the identification of an enrolled member of a population of interest, a graphic user interface page is displayed. In one embodiment, the interface is an "Information" page. That page or user interface screen contains information on each prior session where all previously completed forms can be reviewed. Since names are not typically retained (although they could be using the Name field in the form) there is no absolute way to access a particular individual's data except by fingerprint. There is, however, a method to access ad-hoc individual information based on the unique ID value (record #) that is issued to each individual. When the reporting is completed, useful aggregated data can be retrieved directly from the database by an authorized user using Microsoft Access or other ODBC compliant database application.

Figure 4A:
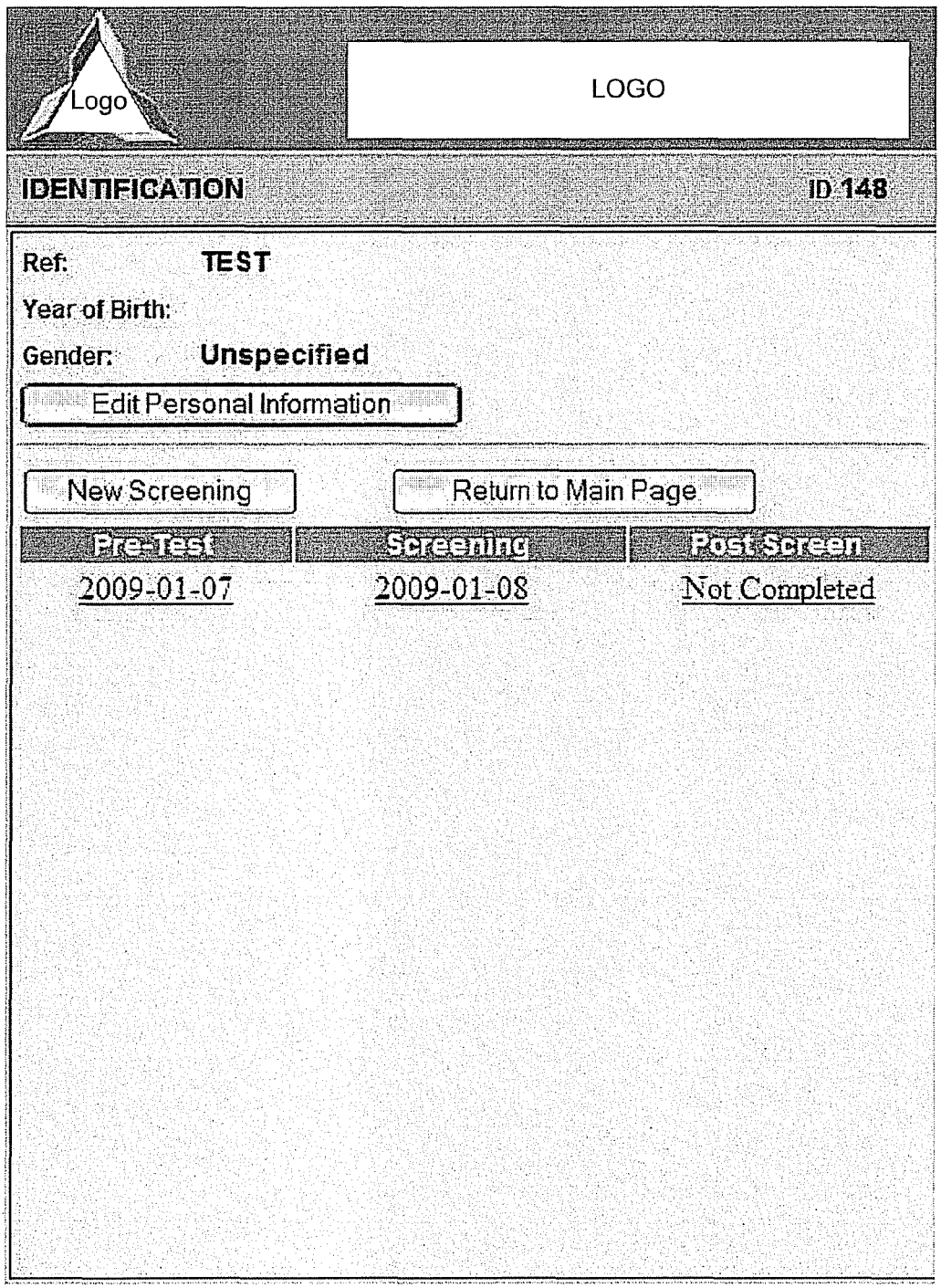

When a fingerprint (or other biometric identifier) is scanned, sent to the server and recognized, the user arrives at the "Identification" page, as shown in FIG. 4A, showing previous data acquisition sessions and dates, in accordance with one embodiment. This page also allows for creating a new session. Clicking on any date link retrieves the previously stored data. A newly enrolled fingerprint (scanned template) will have no dated entries (no data acquisition sessions).

Figure 4C:
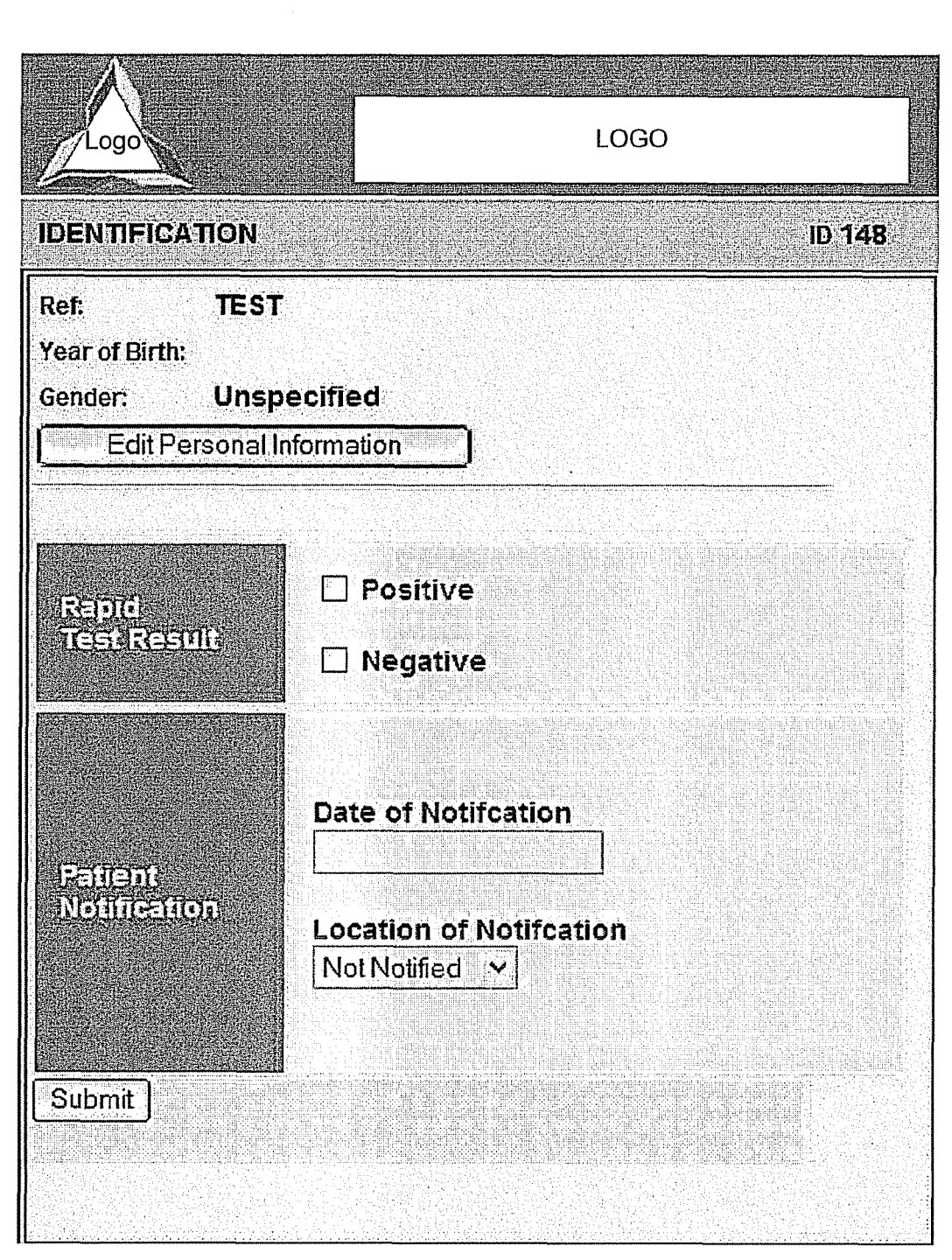
Figure 4D:

Creating a new data acquisition session requires entering data into each form in this exemplary embodiment in a pre-set order (pre-screening questionnaire, screening and post-screening questionnaire). FIG. 4B shows an exemplary pre-test counseling and questionnaire form. FIG. 4C shows an exemplary identification screening form. FIG. 4D shows an exemplary post-test questionnaire, which can include questions about the individual's medical history. In other embodiments the sequence of forms completion may be customized to be any in any suitable order that varies from application to application.

Specific Non-Limited Uses and Examples

The method, device, and system embodiments described herein facilitate the collection of personal data from members of a population of interest at remote locations such that the personal data can be stored at one or more locations while maintaining the anonymity of the individual members of the population that contribute to the overall data regarding the population.

In light of these features, the embodiments described herein can be extended to various fields of interest. Specifically, the personal data collection and confidentiality maintain features of the present invention are amenable to use in all of the following:
  Healthcare management
  Homeland Security
  Double-blind research projects
  Pharmaceutical trials,
  Marketing & product preference trials
  Census data collection
  Research on drug addict populations
  Follow-up care for health care independent of location of delivery Remote field research
Crisis & emergency record management
Parole/probation management system
Event or program participation/attendance management
Standardized testing data collection
and various other fields and disciplines in which remote data acquisition and confidentiality and/or anonymity are potential concerns or requirements Report Example I

| male | female | Residence | People in Household | Education | Languages Spoken | Occupation | YOB |
|---|---|---|---|---|---|---|---|
|  | 1 | Village A | Mother/Sister/Brother | Grade 1 | Siswati | Unemployed | 1981 |
|  | 1 | Village A | Brother/ | Grade 10 | Siswati/English | Student | 1982 |
|  | 1 | Village A | Grandmother/Brother | Grade 12 | English/Xitsonga | Unemployed | 1983 |
|  | 1 | Village A | Father | Grade 12 | Siswati/English | Unemployed | 1981 |
| 1 |  | Village B | Mother | Grade 6 | Siswati/ | Unemployed | 1981 |
|  | 1 | Village A | Grandfather/Husband | Grade 1 | Xitsonga | Unemployed | 1981 |
|  | 1 | Village A | Husband/Son/Daughter | Grade 1 | Xitsonga | Unemployed | 1987 |
|  | 1 | Village A | Son/Daughter | Grade 1 | Xitsonga | Unemployed | 1983 |
|  | 1 | Village A | Brother/Son | Grade 1 | Xitsonga | Unemployed | 1981 |
| 1 |  | Village C | Wife/Son/Daughter | Grade 11 | Siswati | Unemployed | 1981 |
|  | 1 | Village C | Son/Daughter | Grade 1 | Xitsonga | Unemployed | 1981 |
|  | 1 | Village A | Husband | Grade 1 | Siswati | Unemployed | 1987 |
|  | 1 | Village C | Husband | Grade 1 | Siswati | Unemployed | 1981 |
| 1 |  | Village A | Mother/Sister/Brother | Grade 11 | Siswati |  | Student | 1984 |

Non-Limiting Software Features and Embodiments for Implementing Anonymous Biometric Identifier User Data Collection In one embodiment, the invention relates to systems, methods, and devices that facilitate anonymous personal data collection using a mobile device, and enable automatic (or user controlled) processing (or archiving) and securing of personal data using the mobile device (or workstation or other processor-based device). In part, one embodiment relates to collecting personal data such that it is paired or associated with a biometric identifier for secure and confidential storage in a database. According to one embodiment, device-generated personal data, and biometric identifiers are also stored, processed, and transmitted.

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as biometric data, user data, patient data, date of birth, treatment regimen, date of infection, one or more fingerprints, a file associated with a member of a population of interest, and other information of interest described herein.

The device, software, methods, and systems described herein can incorporate various network-based technologies. In various embodiments, suitable network-based technologies for transmitting and receiving personal data and biometric identifiers and processed versions in thereof include, but are not limited to cellular, TCP/IP, infrared (IR), satellite, Bluetooth, wide area network (WAN) and WLAN, Wireless Fidelity (Wi-Fi) such as 802.x standardized systems and are to be used generically when referring of any type of 802.11 network, whether WEE 802.11b, 802.11a, 802.11g, 802.11n, 802.16, 802.20 dual-band, GPRS, CDMA, EDGE, WCDMA, CDMA2000, TD-SCDMA network, UWB/W-USB, ZigBee, NFC, LTE and WiMax.

Embodiments may operate over current mobile communication networks based on either Code Division Multiple Access (CDMA) or Global Systems Mobile (GSM) standards, or other systems. The device network and the Internet can be accessed using various protocols and auxiliary networks, including the suitable network-based technologies discussed above.

In addition to the client application resident on the mobile device, an overall service including certain hardware components, such as servers that act as processing or personal data storage elements can also be established to facilitate the transfer and processing of personal data and biometric identifiers for a person of interest in a population of interest. Servers suitable for performing the processing, routing, transmission, and archiving of personal data and biometric identifiers can use a Windows-based operating system, a Mac based, a Linux-based operating system, or any other suitable open source or proprietary operating system.

The servers may have any suitable hardware configurations configured to support the database and anonymity maintaining features and the storage and remote access functionality of the invention. The servers may be wireless or LAN-based. Blade servers can be used in one embodiment.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), SSD (Solid State disc), memory stick, ROM (read only memory), RAM (random access memory), DRAM (dynamic random access memory), PROM (programmable ROM), EEPROM (extended erasable PROM), a PC card (e.g., PCMCIA card), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The present invention may be embodied in may different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC), or any other means including any combination thereof. In a typical embodiment of the present invention, some or all of the processing of the data collected using the interface and biometric scanner along with the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for anonymizing user data, generating a biometric template, enrolling a user at a remote location, generating a target database of user profiles that have a common characteristic, such as a disease state, and otherwise detecting or displaying any of the foregoing and all of the other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as FORTRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

I claim:

1. A method of remote data collection and remote user identification comprising the steps of:
   providing a mobile device comprising a biometric scanner, memory, a display, and a processor;
   identifying a plurality of members of a population of interest based upon a characteristic;
   acquiring a biometric identifier from a member of the population of interest using the biometric scanner at a first location that lacks internet connectivity;
   converting the biometric identifier to a template;

anonymously collecting personal data relating to a sensitive condition from the member of the population of interest at the first location;
storing the template and the personal data locally on the mobile device when internet connectivity or cellular telephone signal is unavailable;
transmitting the locally stored template and personal data using the mobile device to a server located at a second location with respect to which the first location is remotely located when a cellular telephone signal or internet connectivity is available;
automatically deleting the locally stored template and personal data from the mobile device after transmitting the locally stored template and personal data;
storing the personal data such that the personal data is indexed only using the biometric identifier; and
automatically generating a report relating to the sensitive condition, the characteristic, and the first location based on anonymously collected personal data of a plurality of members of the population of interest at the first location.

2. The method of claim 1 wherein the mobile device is selected from the group consisting of a laptop, a personal digital assistant, a smart phone, and a messaging device.

3. The method of claim 1 wherein the biometric identifier is selected from the group consisting of a fingerprint, a retinal scan, and other personal identifier suitable for scanning and electronic transmission and storage.

4. The method of claim 1 wherein the sensitive condition is a disease state and the first location is a rural location or a location without electricity.

5. The method of claim 1 further comprising the step of anonymously enrolling the plurality of members of the population of interest in a population study using the biometric identifier acquired for each member of the population of interest.

6. The method of claim 5 further comprising the step of searching a database that comprises anonymous personal data associated with enrolled members of the population of interest only in response to transmission of a vectored template of a fingerprint of an enrolled member and tracking changes in the population of interest over time by updating each member's personal data using data collected after identifying a member using their biometric identifier.

7. The method of claim 5 further comprising the step of generating a report relative to an anonymous population of interest, each anonymous member of the population of interest having a data file and biometric identifier stored in a database, wherein the stored biometric identifier comprises one or more relationships between reference points and paths connecting the reference points, wherein the reference points are generated from a scan of a fingerprint.

8. A mobile device-based individual data collection and transfer system comprising:
a data entry interface of a mobile device, the mobile device comprising a transmitter, a receiver, and a processor, the data entry interface configured to collect anonymous personal data comprising a sensitive condition;
a biometric scanner in electronic communication with the data entry interface of the mobile device, the processor for receiving biometric data from the biometric scanner, the processor receiving the anonymous personal data generated using the data entry interface;
wherein a biometric identifier is generated using the biometric scanner and is paired with the anonymous personal data using the mobile device such that the anonymous personal data can be stored anonymously at a remote location;
an electronic memory device, wherein the memory device comprises instructions that when executed by the processor cause the processor to:
store the anonymous personal data locally in the electronic memory when internet connectivity or cellular telephone signal is unavailable and delete the personal data after it has been transmitted to the remote location;
a server comprising software that enrolls members of a population of interest in a study in response to the biometric identifier received from the mobile device, the server located at the remote location; and
a database configured to store a plurality of member files comprising anonymous personal data, each member file associated with a unique biometric identifier for that member, the database accessible using the biometric scanner and the data entry interface such that enrolled members of the population of interest can be identified and data entry be performed with respect to such members at a location remote from the server.

9. The system of claim 8 further comprising a diagnostic test kit for generating test results such that the test results comprise an element in the anonymous personal data, wherein the location remote from the server is a rural location or a location without electricity.

10. The system of claim 8 further comprising an anonymizing module that executes using the processor that processes user data and restricts the transmission of personal identifiable information.

11. The system of claim 8, wherein the server comprising software that enrolls members of the population of interest in response to a biometric identifier received from the mobile device.

12. The system of claim 8 wherein the database is searchable using biometric identifier templates of anonymous members of the population of interest.

13. The system of claim 8 wherein the data entry interface is programmed to display fields and receive inputs specific to a data collection scheme, the data collection scheme selected from a group consisting of baseline education surveys, user registration, concert admission, medical data collection, census data collection, HIV screening, user enrollment, and data collection relating to a population of interest with sensitive information that requires confidential storage.

14. A method for anonymously collecting information from a member of a population of interest, the method comprising the steps of:
surveying a population of interest with regard to a sensitive condition at a remote location that lacks internet connectivity;
acquiring a biometric identifier from each member of a plurality of members of the population of interest using a biometric scanner at the remote location;
anonymously enrolling members of the population of interest having the sensitive condition at the remote location using their respective biometric identifier;
anonymously collecting personal data from the enrolled member during a data collection session, the personal data relating to the sensitive condition;
generating a time stamp for the data collection session;
associating the member's biometric identifier with the member's personal data;

anonymously transmitting the personal data to a database using a cellular telephone signal at the remote location; and storing the personal data in the database such that the personal data is indexed only using the biometric identifier such that the personal data remains anonymous.

15. The method of claim 14, wherein the biometric identifier is acquired as a vectored template comprising one or more relationships between a plurality of points and paths connecting the plurality of points.

16. The method of claim 15 further comprising the step of searching the database to locate the personal data in response to transmission of a vectored template corresponding to the biometric identifier of the enrolled member; and tracking members of the population of interest over time by periodically collecting data and associating such data with the vectored template.

17. A computer system for anonymously collecting information from a member of a population of interest at a remote location, the computer system comprising:
an electronic memory device; and
an electronic processor in communication with the memory device, wherein the memory device comprises instructions that when executed by the processor cause the processor to:
anonymously enroll a member of the population of interest in a study by acquiring a biometric identifier from the member at the remote location that lacks internet connectivity;
convert the biometric identifier acquired from a member of a population of interest into a vectored template;
associate the vectored template with anonymous personal data collected from the member, the anonymous personal data relating to a sensitive condition, wherein the vectored template comprises one or more relationships between a plurality of points and a plurality of paths connecting the plurality of points, the plurality of points obtained from a scan of a biometric identifier; and
transmit the anonymous personal data to the electronic memory device using a cellular telephone signal.

18. The system of claim 17 wherein the memory device comprises instructions that when executed by the processor cause the processor to execute an anonymizing module that processes user data and restricts the transmission of personal identifiable information.

19. The system of claim 17 comprising a server and a database, the server comprising software that anonymously enrolls members of the population of interest in response to the vectored template received from the electronic memory device, the database storing a plurality of member files, each member file associated with a unique biometric identifier, wherein the server and database are located at one or more locations with respect to which the population of interest is remotely located.

20. The system of claim 19 wherein the database is searchable using biometric identifier templates of anonymous members of the population of interest and further comprising report generating software configured to automatically generate a report relating to the sensitive condition.

21. One or more non-transitory tangible computer readable media encoded with software, the software comprising computer-readable instructions operable, when executed, to cause one or more processors to:
anonymously enroll a member of a population of interest at a remote location that lacks internet connectivity using a biometric identifier;
collect personal data relating to a sensitive condition of the member of the population of interest at the remote location;
time stamp each data collection session at the remote location;
convert the biometric identifier acquired from the member of the population of interest into a vectored template;
associate the vectored template with personal data collected from the member of the population of interest;
the personal data being anonymized such that the member's identity is not transmitted with the personal data;
transmit the personal data at the remote location using a cellular telephone signal to an electronic memory device comprising a database to store the personal data, the electronic memory device located at a facility with respect to which the population of interest is remotely located; and
perform statistical analysis relative to an anonymous data set of personal data collected from a plurality of members of the population of interest to generate one or more of a treatment report or a disease trajectory report for the population of interest; and
display one or more of the treatment report or disease trajectory report.

22. The tangible media of claim 21 wherein the software comprises computer-readable instructions operable, when executed, to cause one or more processors to retrieve the personal data only in response to the biometric identifier being scanned during a subsequent data collection.

* * * * *